United States Patent [19]

Payton Hugh W.

[11] Patent Number: 4,857,058
[45] Date of Patent: Aug. 15, 1989

[54] SUPPORT PATCH FOR INTRAVENOUS CATHETER

[76] Inventor: Payton Hugh W., 36 S. Main St., Jeffersonville, Ohio 43128

[21] Appl. No.: 217,247

[22] Filed: Jul. 11, 1988

[51] Int. Cl.⁴ .............................................. A61M 5/00
[52] U.S. Cl. ............................ 604/180; 128/DIG. 26
[58] Field of Search ..................... 604/180, 174, 179; 128/DIG. 26

[56] References Cited

U.S. PATENT DOCUMENTS 4,579,120  4/1986  MacGregor .............. 128/DIG. 26
4,711,636  12/1987  Bierman ............................ 604/180

Primary Examiner—Stephen C. Pellegrino
Attorney, Agent, or Firm—Biebel, French & Nauman

[57] ABSTRACT

An intravenous needle support patch for supporting the head of an infusion needle while protecting the wound from infection includes a first flat section formed of plastic material and a second flat section also formed of plastic material and pivotally joined with the first section, so that the two sections may be spread apart or closed together about a common parting line. One of the two sections, offset from the parting line, is formed with a pair of upstanding posts for receiving the head of an intravenous needle therebetween. A diagonal opening is formed between the sections at the parting line, permitting the infusion needle to pass therethrough. The patch is formed with lines of weakness to provide flexibility and is further formed with tube-receiving posts at the corners for supporting the infusion tube independently of the needle head.

7 Claims, 2 Drawing Sheets

SUPPORT PATCH FOR INTRAVENOUS CATHETER

This application relates to the protection and support of intravenous catheters, and more particularly to a support or patch which stabilizes the catheter and protects the wound.

Typically intravenous catheters and the attendant infusion tubing are retained and held, after placement, by tape and bandage. Such technique is haphazard at best, and at worst, the wound may not be properly protected, and the intravenous catheter may not be properly positioned and stabilized.

Attempts to provide an appliance in the form of a patch have met with indifferent success. The various patches or appliances have either been difficult to apply, have failed to provide adequate support for the catheter and/or tubing, or have failed to provide adequate protection for the wound.

SUMMARY OF THE INVENTION

This invention relates to an intravenous support patch which is particularly adapted for application to the skin of a patient for the stabilization of a flexible catheter. The patch of this invention is formed in two sections or parts joined at a pivot or hinge, and is closable about a slit or parting line which intersects the axis of the catheter.

The patch is provided with a pair of upstanding supports which are spaced apart to receive the catheter head therebetween with the flexible hollow needle extending diagonally between the sections. For stability, these supports, in the form of posts, are supported or formed on the upper surface of only one of the two parts of the patch. An inclined opening leading from the needle head supports is formed at the parting line, and is proportioned so that when the two parts of the patch are brought together, the parts may close about the flexible catheter tube and enclose the tube without pinching it.

The patch is formed with hinges or thinned portions which extend longitudinally as well as laterally with respect to the posting line. The hinge lines thus formed provide flexibility about intersecting axes, to provide ease of conformity with the contour or shape of the body, at the catheter, Thus, the lines of flexibility or weakness permit the patch to curve and to conform comfortably to the hand or to an arm.

Each of the halves of the patch are further formed with pairs of upstanding posts which are spaced so as to support the infusion tube at various locations, and to prevent strain on the tube from being carried to the catheter.

Removable protector tape or strips protect an attachment adhesive on the patch bottom. These strips are easily removed after the patch is substantially in place, by pealing off to expose the adhesive surface.

The hinged connection of the two halves of the patch assures an accuracy of alignment of the parts, when closed about the infusion needle. It also insures the proper alignment of the catheter head and provides support for the tubing.

An important object of the invention is the provision of an intravenous patch, as outlined above, which is easy to apply and which provides an assured positioning of the parts of an intravenous administration.

Another object of the invention is the provision of an intravenous patch is formed in two pivotally-attached halves or parts which parts open and close about a parting line, and which includes an inclined catheter opening in the plane of the parting line. An advantage of the arrangement is the fact that, in the preferred embodiment, the needle head support posts are formed on just one of the patch parts, to permit the support of the catheter at the desired location before the parts are closed about the catheter.

A further object and advantage of the invention is the provision of a patch as outlined above, in which bend lines or lines of flexibility are formed in the parts, to permit bending in both longitudinal and lateral directions, to conform to the body contour.

Another advantage of the invention permits the support of the intravenous tube, apart from the support of the catheter and catheter head, in a plurality of the locations on the patch.

These and other objects and advantages of the invention will be apparent from the following description, the accompanying drawings and the appended claims.

BRIEF DESCRIPTION OF ACCOMPANYING DRAWINGS

DESCRIPTION OF PREFERRED EMBODIMENT

Figure 1:
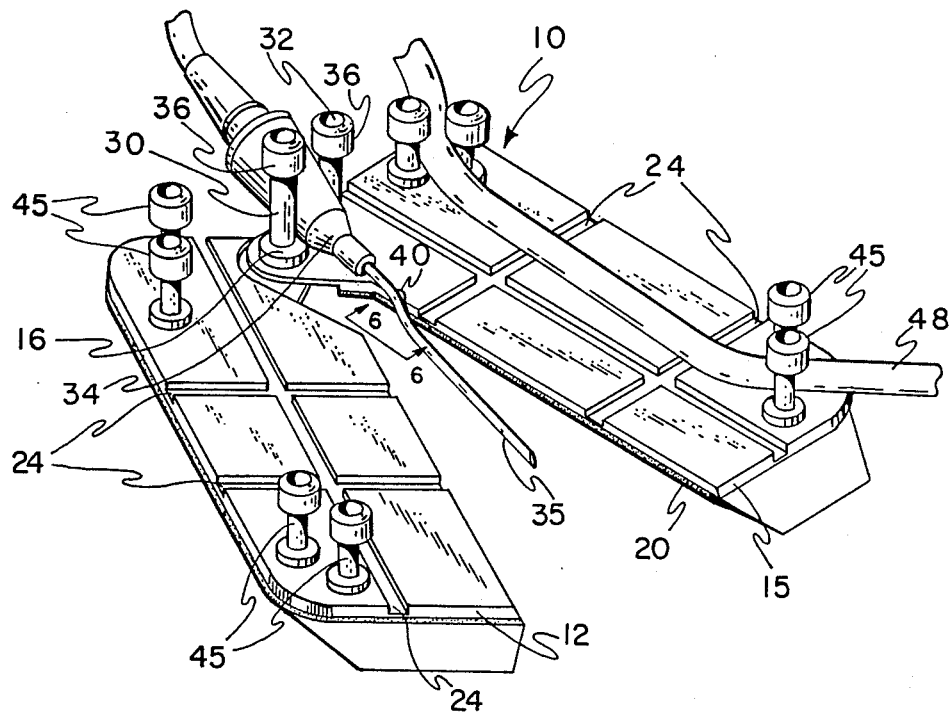
FIG. 1 is a perspective view of a patch made according to this invention, showing the patch halves open or spread apart about the pivot with the catheter head in place.

Referring to the figures of the drawing, which illustrate a preferred embodiment and the best mode contemplated by the application, a patch 10 is illustrated as having a first half or section 12 and a pivotally attached second half or section 15. The sections 12 and 15 are formed of plastic material, such as medical grade vinyl. The parts are pivotally attached at a laterally offset hinge rivet 16, and define therebetween a common parting line 20. Each patch section is generally rectangular in shape, and together make a completed patch of approximate square shape.

Figure 3:
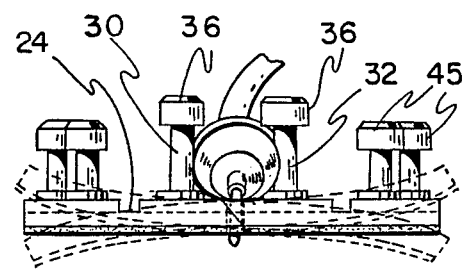
FIG. 3 is an end elevation of the patch, and showing in broken lines one degree of flexibility thereof.
Figure 4:
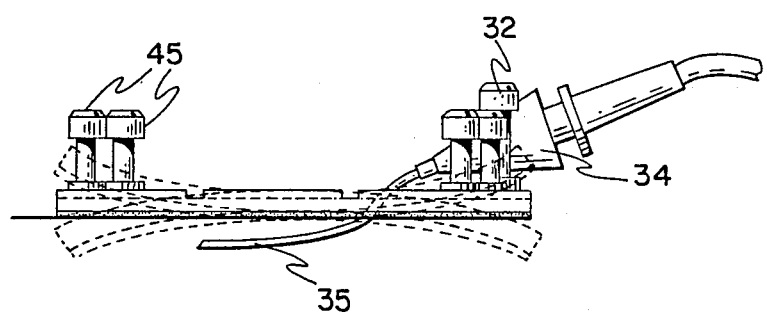
FIG. 4 is a side elevation of the patch and showing in broken lines another degree of flexibility.

The principal body portions of each of the sections are formed as a relatively thin sheet of plastic. To add to the flexibility, lines of weakness or score lines 24 are formed in the upper surfaces thereof, with two of the lines running generally parallel to the parting line 20, and two of the lines running lateral or transverse to the parting line. The lines 24 in effect form integral hinges, enhancing the flexibility of the patch in two directions, as illustrated by the broken line positions of the parts in FIGS. 3 and 4.

Figure 2:
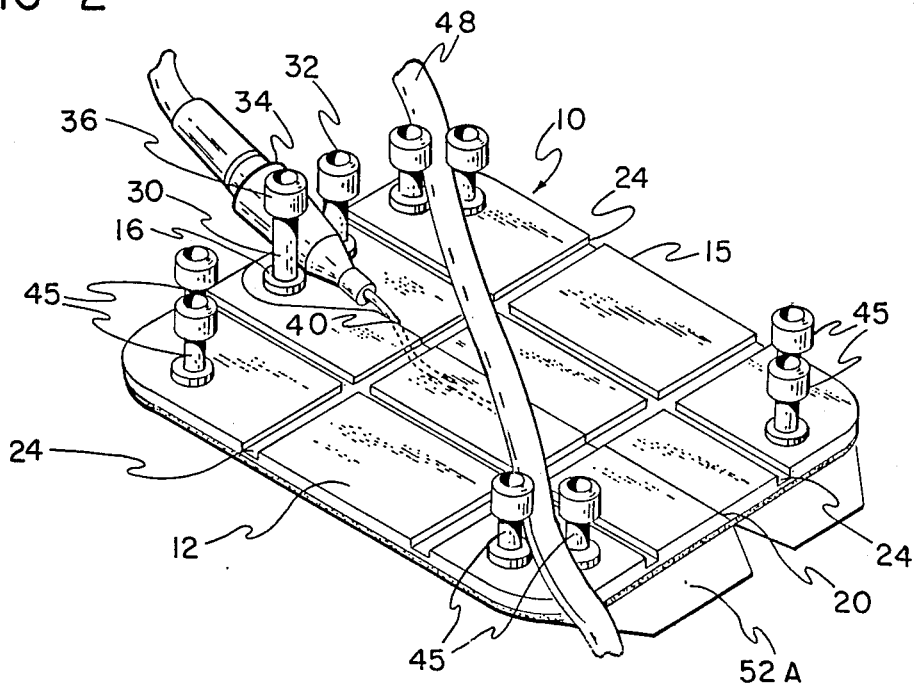
FIG. 2 is a perspective view of the patch after the halves have been closed about the catheter.
Figure 6:
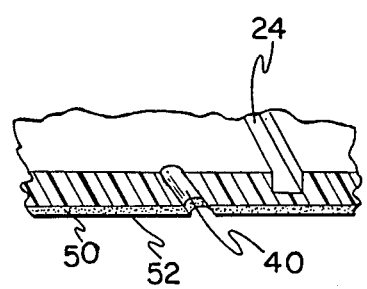
FIG. 6 is a fragmentary view showing the needle access opening at the parting line.

As perhaps best shown in FIG. 1, the parting line 20 runs straight between the section 12 and 15 over a major portion of the length thereof, and is then offset laterally so as to include the pivot rivet 16 in the section 15. This permits two catheter head stabilizing posts 30 and 32 to be placed or carried entirely on the section 15. The post 30 may be an extension of the rivet 16. The posts 30 and 32 are spaced to receive and support the head 34 of a flexible intravenous administration catheter 35 therebetween, and are formed with somewhat enlarged retainer heads 36 on the top. Each section 12 and 15, at the parting line 20, forms half of a catheter access opening 40 (FIG. 6). The opening 40 slopes on a diagonal between the head support posts 30, 32 and the bottom surface of the patch, in general alignment with the axis of the head 34 and provides a fixed or defined location for the hollow catheter needle 35 in relation to the catheter head 34. When the parts 12 and 15 are closed about the line 20, as shown in FIG. 2, the catheter is stabilized in the ideal position.

Additional pairs of posts 45 are integrally formed on the respective base portion and extend upwardly to form receptors for the flexible infusion tube 48 therebetween. The post pairs 45 are located at each of the four corners, and provide versatility in the support of the tube 48. When the tube is so supported on the patch, as shown in FIGS. 1 and 2, the catheter head 34 rests between the posts 30 and 32 free of strain.

Figure 5:
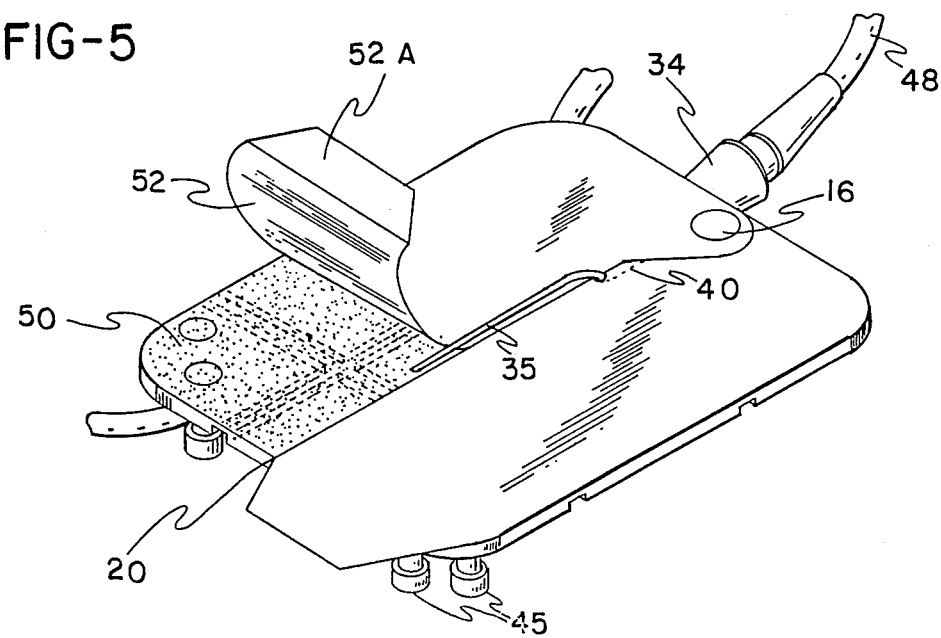
FIG. 5 is a perspective view of the patch from the bottom.

The bottom surfaces 50 of the parts, as shown in FIG. 5, is coated with a medical grade adhesive. The adhesive may be protected by release paper 52, and a tab or portion 52a of the paper 52 may extend beyond the bottom surfaces 50, for ease of gripping and removal to expose the adhesive surface, during the application of the patch.

In use, the intravenous catheter is properly located and the flow started. When is it determined that the intravenous administration is functioning properly, the protective patch 10 of this invention may be applied. The patch 10 is brought over the wound as shown in FIG. 1, and the head 34 carefully inserted between the stabilizing posts 30 and 32. The flexible catheter 35 should be checked to be sure that it rests in the access opening 40 without pinching. The two halves 12 and 15 may now be brought together, by pivoting about the rivet 16, to close the parting line 20, as shown in FIG. 2. Now the adhesive protector paper or strips 52 may be pealed off, by pulling the paper back upon itself. When the patch is then pressed to the skin, the wound at the catheter entrance is effectively protected. The free portion of the tube 48 may be stabilized by insertion into one or more pairs of the supplemental support posts 45, so as to relieve any stain from the catheter, as shown in FIG. 2.

While the form of apparatus herein described constitutes a preferred embodiment of this invention, it is to be understood that the invention is not limited to this precise form of apparatus, and that changes may be made therein without departing from the scope of the invention which is defined in the appended claims.

What is claimed is:

1. An improved support patch for the protection and support of an infusion intravenous catheter, comprising:
   a first patch section and a second patch section,
   means on said sections defining a common parting line therebetween,
   pivot means joining said sections together for opening and closing movement about said common parting line,
   means on an upper surface of one of said sections for supporting the head of an infusion catheter with the needle thereof extending diagonally between said sections, said sections being movable about said pivot means to close about an infusion needle at said parting line, and
   adhesive on the bottom surfaces of said sections for supporting said patch on the skin.

2. The patch of claim 1 in which said means for supporting the head of an infusion needle comprises a pair of spaced posts rigidly formed on the upper surface of said one section, said posts being positioned adjacent said pivot means.

3. The patch of claim 1 further comprising a plurality of pairs of tube support posts formed on the upper surface of said sections and proportioned to support an infusion tube therebetween.

4. The patch of claim 1 further comprising means at said parting line defining a diagonal needle receiving opening formed partially in each of said sections for receiving said catheter needle therethrough.

5. An improved intravenous needle support patch for supporting the head of an infusion needle while protecting the wound from infection, comprising:
   a first generally flat section formed of plastic material with an upper surface and a lower surface, and defining the first half of a parting line along an edge thereof,
   a second generally flat section formed of plastic material with an upper surface and a lower surface and defining a second half of said parting line along an edge thereof,
   pivot means mounting said sections together for pivotal movement relative to each other between an open position at which said sections are spread apart at said parting line and a closed position at which said sections are abutting along said parting line,
   means on the upper surface of said patch defining a pair of needle head support posts positioned to support the head of an infusion needle with the flexible infusion portion thereof extending between said sections at said parting line and extending below the bottom of said patch, and
   a medical grade adhesive on said patch section bottoms.

6. The patch of claim 5 in which said pivot means is a rivet and is offset laterally from said parting line, and said posts are formed exclusively on one only of said sections adjacent said rivet.

7. The patch of claim 6 in which one of said posts is integral with said rivet.

* * * * *